United States Patent [19]
Gross et al.

[11] Patent Number: 4,865,838
[45] Date of Patent: * Sep. 12, 1989

[54] COMPOSITION FOR SETTING THE HAIRDO AND GROOMING THE HAIR

[75] Inventors: Paul Gross, Darmstadt; Udo Wiegand, Weiterstadt, both of Fed. Rep. of Germany

[73] Assignee: Wella Aktiengesellschaft, Darmstadt, Fed. Rep. of Germany

[*] Notice: The portion of the term of this patent subsequent to Nov. 1, 2005 has been disclaimed.

[21] Appl. No.: 57,706

[22] Filed: Jun. 1, 1987

Related U.S. Application Data

[63] Continuation of Ser. No. 767,793, filed as PCT EP84/00422 on Dec. 21, 1984, published as WO85/02999 on Jul. 18, 1985, abandoned.

[30] Foreign Application Priority Data

Jan. 13, 1984 [DE] Fed. Rep. of Germany ....... 3401037

[51] Int. Cl.$^4$ .................. A61K 7/06; A61K 7/11; A61K 7/13; A61K 9/12
[52] U.S. Cl. .................................. 424/47; 8/405; 8/406; 424/DIG. 1; 424/DIG. 2; 424/DIG. 4; 424/70; 424/78; 424/80
[58] Field of Search .................................. 424/47, 70

[56] References Cited

U.S. PATENT DOCUMENTS

| | | | |
|---|---|---|---|
| 3,954,960 | 5/1976 | Valan | 424/47 |
| 3,958,581 | 5/1976 | Abegg et al. | 424/47 |
| 4,009,256 | 2/1977 | Nowak, Jr. et al. | 424/70 |
| 4,445,521 | 5/1984 | Grollier et al. | 424/70 |

FOREIGN PATENT DOCUMENTS

| | | |
|---|---|---|
| 2251307 | 6/1975 | France . |
| 1584127 | 2/1981 | United Kingdom . |
| 2098226 | 11/1982 | United Kingdom . |

OTHER PUBLICATIONS

Seifer-Ole-Fetle-Wachse, *Jahrgang*, 99, #12(1), Jun. 1973, pp. 333-337.

*Primary Examiner*—Dale R. Ore
*Attorney, Agent, or Firm*—Michael J. Striker

[57] ABSTRACT

Composition for setting the hairdo and grooming of the hair on the basis of a synergistic combination of (a) 0.1 to 10.0% by weight of a quaternized copolymerisate consisting of vinyl pyrrolidon and dimethyl aminoethyl methacrylate (80:20) and (b) 0.1 to 5.0% by weight tetraoxyethylene lauryl ether.

By corresponding tests it is shown that other fatty alcohol polyoxyethylene ether than tetraoxyethylene lauryl ether with the component (a) do not show a synergistic effect reinforcement.

5 Claims, No Drawings

COMPOSITION FOR SETTING THE HAIRDO AND GROOMING THE HAIR

This application is a continuation of application Ser. No. 767,793, filed as PCT EP84/00422 on Dec. 21, 1984, published as WO85/02999 on Jul. 18, 1985, now abandoned.

It is an object of the invention to provide a composition for setting the hairdo and grooming the hair which contains tetraoxyethylene laurylether and a quaternized copolymerisate of vinyl pyrrolidone with dimethyl amino ethyl methacrylate (80:20).

Compositions for setting the hairdo and grooming the hair customarily consist of solvents of film forming natural or synthetic polymers. As natural polymers one considers, for example, shellac, alginates, gelatines, pektines, chitosan salts and cellulose derivatives. As synthetic polymers one may use, for example, polyvinyl pyrrolidone, polyvinyl acetate, polyacryl compounds, like acrylic acid or methacrylic acid polymerisates, basic polymerisates of esters from these two acids with amino alcohols or the salts or quaternisation products of these basic polymerisates, polyacryl nitrile as well as copolymerisates from such compounds, for example polyvinyl pyrrolidon-vinyl acetate.

Furthermore, compositions for grooming the hair and setting the hairdo and for improving the wet combability and the touch, in particular of damaged hair, very often contain monomer quaternary ammonium compounds like, for example, alkyl trimethyl ammonium chloride, dialkyl dimethyl ammonium chloride, alkyl dimethyl benzyl ammonium chloride and alkyl pyridinium chloride.

However, such quaternary ammonium compounds impair the physiological compatibility of such preparations, in particular the compatibility with the eyes.

In contrast thereto, it was now found that compositions for setting the hairdo and grooming of the hair show a surprising and excellent improvement of the combability of the the hair as well as the setting of the hair on the basis of a watery, alcoholic or watery-alcoholic solution of a film forming resin and an oxethylized fatty alcohol as well as propellants, if need be, and customary additives, characterized that it contains
(a) as a film forming resing 0.1 to 10.0% by weight of a quaternized copolymerisate made from vinyl pyrrolidon and dimethyl aminoethyl methacrylate (80:20) and
(b) as oxethylized fatty alcohol 0.1 to 5.0% by weight tetraoxethylene lauryl ether.

The copolymerisate mentioned under (a) consisting of vinyl pyrrolidon and dimethyl aminoethyl methacrylate should be preferably quaternized with dimethyl sulfate or diethyl sulfate. Particularly suitable as quaternized copolymerisate made from vinyl pyrrolidon and dimethyl aminoethyl methacrylate (80:20) are the commercially available products GAFQUAT®734 and GAFQUAT®755 of GAF Corporation, New York. They have the following formula

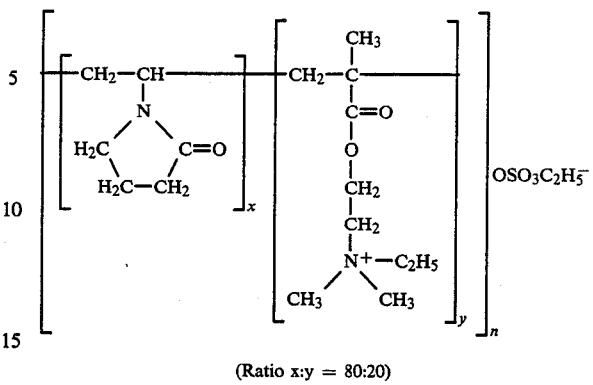

(Ratio x:y = 80:20)

The mean molecular weight with GAFQUAT®734 is about 100 000 and with GAFQUAT®755 about 1000 000 (g/Mol).

Tetraoxyethylene laurylether of the formula $$CH_3(CH_2)_{10}CH_2(OCH_2CH_2)_4OH$$

is the tetraoxyethylene ether of the lauryl alcohol.

In the composition in accordance with the invention the tetraoxyethyllene lauryl ether should be contained in an amount of 0.1 50 5% by weight, preferably in an amount of 0.5 to 2% by weight. The content of the quaternized copolymerisate consisting of vinyl pyrrolidon and dimethyl aminoethyl methacrylate is about 0.1 to 10% by weight, preferably 1 to 3.5% by weight ethylalcohol and isopropylalcohol or mixtures of these two alcohols may be present in the inventive composition in an amount of 0 to 99.8% by weight. Naturally, hair cosmetic additives may be present in the inventive composition, for example, perfume oils, herb extracts, bactericidal or fungicidal substances, antidandruff agents, dissolving intermediary for perfume oils, natural or synthetic resins like chitosan salts, polyvinyl pyrrolidon, polyvinyl pyrrolidonvinyl-acetate-copolymers, as far as such additives appear to be useful and advantageous. Furthermore, coloring agents for coloring the preparation or coloring substances which are applied directly on the hair for a simultaneous tinting of the hair may be present.

Of the latter coloring agents which may be present individually or in a mixture, the following classes may be mentioned by way of example; Aromatic nitro coloring substances. for example, 1,4-diamino-2-nitrobenzol, azo coloring substances, for example, Acid Brown 4 (C.I. No. 14 805), anthrachinon color substances, for example, Disperse Violet 4 (C.I. No. 61 105) and triphenyl methane color substance, for example, Basic Violet 1 (C.I. No. 42 535), whereby the color substances of these classes may have an acid, nonionogenic or basic character depending on the type of their substitutes. Their total concentration is customarily about 0.05 to 2.0% by weight.

The compositions in accordance with the invention can also be filled into a compression container by adding a propellant, whereby the preparation discharges as a foam which can be easily dosaged and comfortably applied to the hair by means of a valve which is provided with an applicator nozzle. Suitable propellants are, for example, light volatile fluoride hydrocarbons, like, for example, difluoride dichlormethane, trichlor monofluormethane or tetrafluoride dichlorethane or lower alkanes, like, for example, n-butane, i-butane and propane or also dimethyl ether as well as gaslike propellants for the pressures under consideration, for example, $N_2$, $N_2O$ and $CO_2$. Advantageously, the propellants are contained preferably in an amount of about 2 to 10% by weight.

As is customary the composition in accordance with the invention is distributed in the towel dry hair in an amount of about 5 to 20 g depending on the density of the hair, after the hair is washed. Subsequently, the hair is combed and immediately dried with a hair drier in a customary manner or is at first wound onto water wave rollers and dried thereafter.

The observed excellent improvement of the combability of the hair and the setting of the hairdo is surprising and synergistically explainable, since the tetraoxyethylene lauryl ether or the quaternized copolymerisate consisting of vinyl pyrrolidon and dimethyl amino ethyl methacrylate applied alone on the hair in a corresponding solution (see test examples C and D) provides only a mediocre and unsatisfactory improvement of the mentioned criteria.

Furthermore, the following test examples E, F, G and H showed that other fatty alcohol polyoxyethylene ether as tetraoxyethylene lauryl ether do not have the required synergistic effect when used in the inventive composition.

The use of quaternary ammonium compositions can be eliminated all together in the composition in accordance with the invention for setting the hairdo and grooming of the hair due to its excellent combability improving effect, unless one adds these composition to the inventive composition in a low concentration of about 0.2% by weight as a conservation agent for obtaining bacterizidal or fungicidal characteristics.

The following examples will explain the subject matter of the invention in more detail.

EXAMPLES

Example 1

Composition in form of a watery solution

| 1,2 g | tetraoxyethylene lauryl ether |
| 2,5 g | copolymerisate consisting of vinyl pyrrolidon an dimethyl aminoethyl methacrylate in a ratio of 80:20, quaternized with diethyl sulfate |
| 96,3 g | water, completely desalted |
| 100,00 g | |

Example 2

Composition in form of a watery-alcoholic solution

| 0,7 g | tetraoxyethylene lauryl ether |
| 2.0 g | copolymerisate consisting of vinyl pyrrolidon and dimethyl aminoethyl methacrylate in a ratio of 80:20, quaternized with diethyl sulfate |
| 20,0 g | ethanol |
| 77,3 g | water, completely desalted |
| 100,0 g | |

Example 3

Composition in form of a gas pressure package

| 1,5 g | tetraoxyethylene lauryl ether |
| 2,5 g | copolymerisate consisting of vinyl pyrrolidon and dimethyl aminoethylene methacrylate in a ratio of 80:20, quaternized with diethyl sulfate |
| 10,0 g | isopropanol |
| 86.0 g | water, completely desalted |
| 100,0 g | |

Example 4

Composition in form of a pressure gas package

| 1,4 g | tetraoxyethylene lauryl ether |
| 2,0 g | copolymerisate consisting of vinyl pyrrolidon and dimethyl aminoethyl methacrylate in a ratio 80:20, quaternized with diethyl sulfate |
| 8,0 g | ethanol |
| 88,6 g | water, completely desalted |
| 100,0 g | |

Example 5

Composition in form of a watery-alcoholic solution

| 1,20 g | tetraoxyethylene lauryl ether |
| 2,50 g | copolymerisate consisting of vinyl pyrrolidon and dimethyl aminoethyl methacrylate in a ratio of 80:20, quaternized with diethyl sulfate |
| 0,50 g | polyvinyl pyrrolidon |
| 0,05 g | Basic Violet 1 (C.I. No. 42 535) |
| 5,00 g | ethanol |
| 90,75 g | water, completely desalted |
| 100,00 g | |

All percentage figures stated in the subject application represent percentages by weight.

TEST EXAMPLES

Test Example A

After a preceding hair wash the towel dried hair of 20 test persons was treated with a composition in accordance with example 1. Ten of the test persons had normal hair. The remaining ten persons had damaged hair and very badly damaged hair. In order to obtain clear results and to eliminate deviating hair qualities from test person to test person, the hair was parted in the middle and 2.5 to 6 g of the composition, depending on the hair density, was applied to the one half of the hair, while the other half remained untreated. Subsequently, each half was independently combed, rolled onto water wave rollers and dried. Finally, the rollers were removed and the hair groomed. The effect of the preparation could be judged by a group of expert hairdressers. An evaluation was performed in accordance with the scheme for the compiled citeria of the wet combability, durability of the hairdo, curlability, luster, touch and the static charge of the hair:

| Grading: | 1 = | very good |
| | 2 = | good |
| | 3 = | sufficient |
| | 4 = | insufficient |

The result of the test for the treated half of the hair in comparison to the untreated half of the hair is shown in the following table 1.

TABLE 1

|   | Grade 1 | Grade 2 | Grade 3 | Grade 4 |
|---|---|---|---|---|
| Number of the test persons | 16 | 3 | 1 | 0 |

Test Example B

The hair of a further group of 18 test persons were treated with a composition in accordance with example 3 in the same manner as in test example A. Ten persons of the group had damaged and very damaged hair. The remaining 8 persons had normal hair. The results of this test are compiled in the following table 2.

|   | Grade 1 | Grade 2 | Grade 3 | Grade 4 |
|---|---|---|---|---|
| Number of the test persons | 13 | 4 | 1 | 0 |

Test Example C

After testing the synergistic effect, the hair of a further test group of 14 persons were treated as described in test example 1, at one half of the hair with a composition in accordance with example 1, however the tetraoxyethylene lauryl ether was replaced by the corresponding amount of water. The other half of the hair remained untreated. 5 test persons had normal hair and 9 persons had damaged hair. the test result is stated in table 3.

TABLE 3

|   | Grade 1 | Grade 2 | Grade 3 | Grade 4 |
|---|---|---|---|---|
| Number of the test persons | 0 | 3 | 6 | 5 |

Test Example D

For a further testing of the synergistic effect a fourth test group of 13 persons, of which six persons had normal hair and 7 persons badly damaged hair were tested in the same manner as described in test example A on one half of the hair with a composition in accordance with example 1, however the composition did not contain quaternized copolymerisate consisting of vinyl pyrrolidon and dimethyl aminoethyl methacrylate (80:20). The quaternized copolymerisate in the composition of example 1 was replaced by the corresponding amount of water. The second half of the hair remained untreated. The result of the test is stated in the following table 4.

TABLE 4

|   | Grade 1 | Grade 2 | Grade 3 | Grade 4 |
|---|---|---|---|---|
| Number of the test persons | 0 | 4 | 4 | 5 |

A comparison of tables 1 or 2 as well as with tables 3 and 4 clearly shows that the combination contained in the composition in accordance with the invention has a synergistic effect in comparison with the individual components.

Test Example E

The hair of a further test group of 10 persons with damaged and badly damaged hair was treated analog with test example A on one half of the hair with a preparation composition in accordance with example 1, wherein the tetraoxyethylene lauryl ether is replaced by the same amount of trioxyethylene stearyl ether. The other side remained untreated. The test result is shown in the following table 5.

TABLE 5

|   | Grade 1 | Grade 2 | Grade 3 | Grade 4 |
|---|---|---|---|---|
| Number of the test persons | 0 | 1 | 8 | 1 |

Test Example F

The hair of a group of 10 test persons with damaged and badly damaged hair were treated analog with test example A on one half of the hair with a preparation composition in accordance with example 1, wherein the tetraoxyethylene lauryl ether was replaced by the same amount of isostearyl alcohol, ethoxylized with 10 Mol ethylene oxide. The other side of the hair remained untreated. The result of the test is shown in the following table 6.

Table 6

|   | Grade 1 | Grade 2 | Grade 3 | Grade 4 |
|---|---|---|---|---|
| Number of the test of persons | 0 | 1 | 5 | 4 |

The aforementioned test examples E and F that among the polyoxyethylene lauryl ethers the tetraoxyethylene lauryl ether has a clear synergestic effect.

Test Example G

A further group of 10 test persons with damaged hair and badly damaged hair were treated analog to the test example A on one half of the hair with a composition in accordance with example 1, wherein the amount of the tetraoxyethylene lauryl ether was replaced by trioxyethylene lauryl ether. The other half of the hair remained untreated. The result of the test is shown in the following table 7.

TABLE 7

|   | Grade 1 | Grade 2 | Grade 3 | Grade 4 |
|---|---|---|---|---|
| Number of the test of persons | 0 | 3 | 6 | 1 |

Test Example H

Also, a test group of 10 persons with damaged hair and badly damaged hair were treated analog to test example A on one half of the hair with a composition in accordance with claim 1, wherein the amount of tetraoxyethylene lauryl ether was replace with pentaoxyethylene lauryl ether. The other half remained untreated. The result is shown in the following table 8.

TABLE 8

|   | Grade 1 | Grade 2 | Grade 3 | Grade 4 |
|---|---|---|---|---|
| Number of the test of the persons | 0 | 3 | 5 | 2 |

The results of the aforementioned tests show that other fatty alcohol polyoxyethylene ether than tetraoxyethylene lauryl ether are not suitable for us in accordance with the invention.

The surprising and excellent synergistic improvement of the hair conditioning characteristics and the very good setting of the hair, in particular with badly damaged hair is limited in accordance with the desired test result to the inventive combination of tetraoxyethylene lauryl ether with a quaternizeed copolymerisate consisting of vinyl pyrrolidon and dimethyl aminoethyl methacrylate (80:20) and cannot be achieved with other fatty alcohol polyoxyethylene ethers.

We claim:

1. Composition for setting of hairdos and grooming of hair, consisting essentially of:
   (a) 0.1 to 10% by weight of said composition of a quaternized copolymerisate made from vinyl pyrrolidon and dimethyl aminoethyl methacrylate in a molar ratio of 80 to 20;
   (b) 0.1 to 5% by weight of said composition of tetraoxyethylene lauryl ether; and
   (c) water, an alcohol selected from the group consisting of ethanol, isopropanol and mixtures thereof, or a mixture of water and the alcohol.

2. The composition according to claim 1, wherein said copolymerisate is quaternized with dimethyl sulfate or diethyl sulfate.

3. The composition according to claim 1, wherein said copolymerisate is contained in an amount from 1 to 3.5% by weight.

4. The composition according to claim 1, wherein said tetraoxyethylene laurylether is contained in an amount from 0.5 to 2.0% by weight.

5. The composition according to claim 1, further comprising 2 to 10% by weight of a propellant selected from the group consisting of n-butane, i-butane, propane, dichlorodifluoromethane, trichloromonofluoromethane, dichlorotetrafluoroethane, dimethylether, $N_2$, $N_2O$ and $CO_2$.

* * * * *